(12) United States Patent
Bell, Jr.

(10) Patent No.: US 12,178,738 B2
(45) Date of Patent: Dec. 31, 2024

(54) REGULATING FLOW FROM A STOMA ON A PATIENT

(71) Applicant: OstoValve LLC, Richmond, VT (US)

(72) Inventor: Robert C. Bell, Jr., St. Johnsbury, VT (US)

(73) Assignee: OstoValve LLC, Burlington, VT (US)

( * ) Notice: Subject to any disclaimer, the term of this patent is extended or adjusted under 35 U.S.C. 154(b) by 1622 days.

(21) Appl. No.: 16/254,453

(22) Filed: Jan. 22, 2019

(65) Prior Publication Data

US 2019/0224037 A1     Jul. 25, 2019

Related U.S. Application Data

(60) Provisional application No. 62/619,444, filed on Jan. 19, 2018.

(51) Int. Cl.
*A61F 5/44*     (2006.01)
*A61F 5/445*     (2006.01)
*A61F 5/448*     (2006.01)

(52) U.S. Cl.
CPC .......... *A61F 5/4405* (2013.01); *A61F 5/4401* (2013.01); *A61F 5/445* (2013.01); *A61F 5/448* (2013.01); *A61F 2005/4455* (2013.01)

(58) Field of Classification Search
CPC ...... A61F 5/4405; A61F 5/4401; A61F 5/445; A61F 5/448; A61F 2005/4455
See application file for complete search history.

(56) References Cited

U.S. PATENT DOCUMENTS

| | | | |
|---|---|---|---|
| 2,586,940 A | | 10/1947 | Graham |
| 4,344,434 A | | 8/1982 | Robertson |
| 4,351,322 A | * | 9/1982 | Prager ............... A61F 5/445 600/32 |
| 4,381,765 A | * | 5/1983 | Burton ............... A61F 5/445 604/277 |
| 4,424,833 A | * | 1/1984 | Spector ............ A61M 39/0606 277/560 |
| 4,634,421 A | * | 1/1987 | Hegemann ......... A61F 2/0009 604/277 |

(Continued)

FOREIGN PATENT DOCUMENTS

| | | |
|---|---|---|
| AU | 2009259925 B2 | 10/2015 |
| AU | 2015246069 B2 | 9/2017 |

(Continued)

*Primary Examiner* — Guy K Townsend
(74) *Attorney, Agent, or Firm* — Downs Rachlin Martin PLLC

(57) ABSTRACT

A medical appliance is configured with material that creates a fluid barrier with interior walls of a stoma on a patient. These configurations may include an annular disc with a stem on one side that inserts into the stoma. The material may reside on the stem, for example, in the form of a replaceable hollow tube that covers at least part of the stem. On the other side, a rotatable spigot inserts into a recess. The rotatable spigot has a first position that forms a flow path through the stem and the annular disc to allow waste to drain from the stoma. In one implementation, the rotatable spigot can couple with a collection device that receives the waste. The patient can return the rotatable spigot to a second position to prevent flow of waste.

15 Claims, 8 Drawing Sheets

(56) References Cited

U.S. PATENT DOCUMENTS

| | | | | |
|---|---|---|---|---|
| 4,804,375 | A * | 2/1989 | Robertson | A61F 2/0013 604/323 |
| 4,834,712 | A * | 5/1989 | Quinn | A61J 15/0061 604/174 |
| 4,863,438 | A * | 9/1989 | Gauderer | A61M 39/0247 604/105 |
| 6,419,699 | B1 * | 7/2002 | Schuessler | F16L 27/04 604/905 |
| 6,712,800 | B2 | 3/2004 | Kanbara | |
| 6,723,079 | B2 | 4/2004 | Cline | |
| 6,872,189 | B2 * | 3/2005 | DeLegge | A61M 39/12 604/910 |
| 6,997,909 | B2 | 2/2006 | Goldberg | |
| 7,001,367 | B2 | 2/2006 | Arkinstall | |
| 7,025,784 | B1 * | 4/2006 | Blom | A61F 2/203 623/14.11 |
| 7,083,597 | B2 * | 8/2006 | Lynch | A61M 39/02 604/174 |
| 7,172,581 | B2 | 2/2007 | Ciok et al. | |
| 7,452,347 | B2 * | 11/2008 | DeLegge | A61J 15/0057 604/910 |
| 7,846,144 | B2 | 12/2010 | Ciok et al. | |
| 8,043,260 | B2 * | 10/2011 | DeLegge | A61M 39/12 604/910 |
| 8,070,737 | B2 | 12/2011 | Cline et al. | |
| 8,100,875 | B2 | 1/2012 | Cline et al. | |
| 8,192,410 | B2 * | 6/2012 | Smith | A61F 5/445 604/327 |
| 8,388,586 | B2 | 3/2013 | Weig | |
| 8,475,356 | B2 | 7/2013 | Feng et al. | |
| 8,845,606 | B2 | 9/2014 | Nguyen-DeMary et al. | |
| 8,900,116 | B2 | 12/2014 | Hanuka et al. | |
| 8,998,867 | B2 * | 4/2015 | Sabeti | A61F 5/4405 604/335 |
| 9,078,759 | B2 | 7/2015 | Erland | |
| 9,226,848 | B2 | 1/2016 | Johansson | |
| 9,498,371 | B2 | 11/2016 | Salama | |
| 9,615,961 | B2 | 4/2017 | Johansson | |
| 9,636,249 | B2 * | 5/2017 | Davies | A61F 5/445 |
| 9,943,436 | B2 | 4/2018 | Nguyen-DeMary et al. | |
| 10,045,877 | B2 | 8/2018 | Weig | |
| 10,166,138 | B2 * | 1/2019 | Cline | A61F 5/445 |
| 10,188,542 | B2 | 1/2019 | Lin et al. | |
| 10,441,455 | B2 | 10/2019 | Eggert et al. | |
| 10,813,787 | B2 | 10/2020 | Dinakara et al. | |
| 10,864,107 | B2 | 12/2020 | Weig | |
| 2002/0077611 | A1 * | 6/2002 | von Dyck | A61F 5/442 604/332 |
| 2010/0174253 | A1 * | 7/2010 | Cline | A61F 5/445 604/328 |
| 2014/0114266 | A1 | 4/2014 | Arcand | |
| 2015/0164679 | A1 * | 6/2015 | Maidl | A61F 5/445 604/332 |
| 2016/0287428 | A1 * | 10/2016 | Eggert | A61F 5/445 |
| 2017/0367870 | A1 | 12/2017 | Mariani | |
| 2018/0235802 | A1 | 8/2018 | Nguyen-DeMary et al. | |
| 2018/0353319 | A1 * | 12/2018 | Bencini | A61F 5/445 |
| 2018/0360643 | A1 | 12/2018 | Aravalli | |
| 2019/0060105 | A1 * | 2/2019 | Cesa | A61F 5/4405 |
| 2019/0201230 | A1 | 7/2019 | Aravalli | |
| 2019/0380860 | A1 * | 12/2019 | Eggert | A61F 5/4405 |
| 2020/0038228 | A1 | 2/2020 | Aravalli et al. | |
| 2020/0038229 | A1 | 2/2020 | Aravalli | |
| 2020/0155338 | A1 * | 5/2020 | Meteer | A61F 5/443 |
| 2020/0397609 | A1 | 12/2020 | Chang | |

FOREIGN PATENT DOCUMENTS

| | | |
|---|---|---|
| AU | 2016225932 B2 | 11/2018 |
| CA | 2725783 C | 7/2017 |
| CA | 2772527 C | 12/2017 |
| CA | 2984082 C | 7/2019 |
| CN | 102596114 B | 10/2014 |
| CN | 106901890 B | 8/2019 |
| CN | 209220642 U | 8/2019 |
| CN | 210542011 U | 5/2020 |
| CN | 210749757 U | 6/2020 |
| EP | 2303201 B1 | 4/2011 |
| EP | 2150218 B1 | 7/2016 |
| EP | 3167851 A1 | 5/2017 |
| EP | 2632396 B1 | 7/2017 |
| EP | 2642958 B1 | 10/2017 |
| EP | 3284448 A1 | 2/2018 |
| EP | 3295903 A1 | 3/2018 |
| EP | 3215075 B1 | 5/2019 |
| EP | 2475340 B1 | 11/2019 |
| EP | 3785681 A1 | 3/2021 |
| ES | 2633665 T3 | 9/2017 |
| ES | 2654588 T3 | 2/2018 |
| GB | 201809053 | 7/2018 |
| GB | 2534012 B | 12/2019 |
| HR | P20171088 T1 | 10/2017 |
| JP | 5367709 B2 | 12/2013 |
| JP | 6640562 B2 | 2/2020 |
| MX | 2010013308 A | 12/2010 |
| PT | 2303201 T | 6/2009 |
| WO | 1996032904 A1 | 10/1996 |
| WO | 2011139499 A1 | 11/2011 |
| WO | 2020174497 A1 | 9/2020 |
| WO | 2020250145 A1 | 12/2020 |

* cited by examiner

REGULATING FLOW FROM A STOMA ON A PATIENT

CROSS-REFERENCE TO RELATED APPLICATIONS

This application claims the benefit of priority to U.S. Ser. No. 62/619,444, filed on Jan. 19, 2018, and entitled "REGULATING FLOW FROM A STOMA ON A PATIENT," the content of which is incorporated by reference herein in its entirety.

BACKGROUND

Surgical procedures often require post-operative access to a patient's body cavity to drain fluids or waste that may cause infection. A "stoma," for example, is an opening to allow waste from the patient's intestines to exit the body following colostomy or ileostomy surgery. The waste collects in a device, like a bag or pouch, that attaches around the stoma or connects to the stoma via a drain tube. This arrangement, while effective, typically affords the patient little control of waste as it drains involuntarily into a collection device attached to the drain tube. Patients may elect to occlude the drain passage with, for example, a plug (in the stoma) or clamp (on the drain tube), however, discomfort may result because the stoma is not meant to tolerate occlusion for long periods of time. Damage to the drain tube may also allow waste to leak before the collection device.

SUMMARY

The subject matter of this disclosure relates to improvements to devices that regulate flow of waste from a stoma or similar port or opening in the body. Of particular interest herein are embodiments with a rotatable valve that allows a patient to control flow of waste. These embodiments may form a seal internal to the stoma. This seal prevents egress of waste material from the stoma. The seal also keeps the device in place and, thus, forecloses the need for any external restraint on the patient. This feature may make the device much less obtrusive and more comfortable for the patient to wear as they go about their daily activities.

DRAWINGS

Reference is now made briefly to the accompanying figures, in which.

Figure 1:
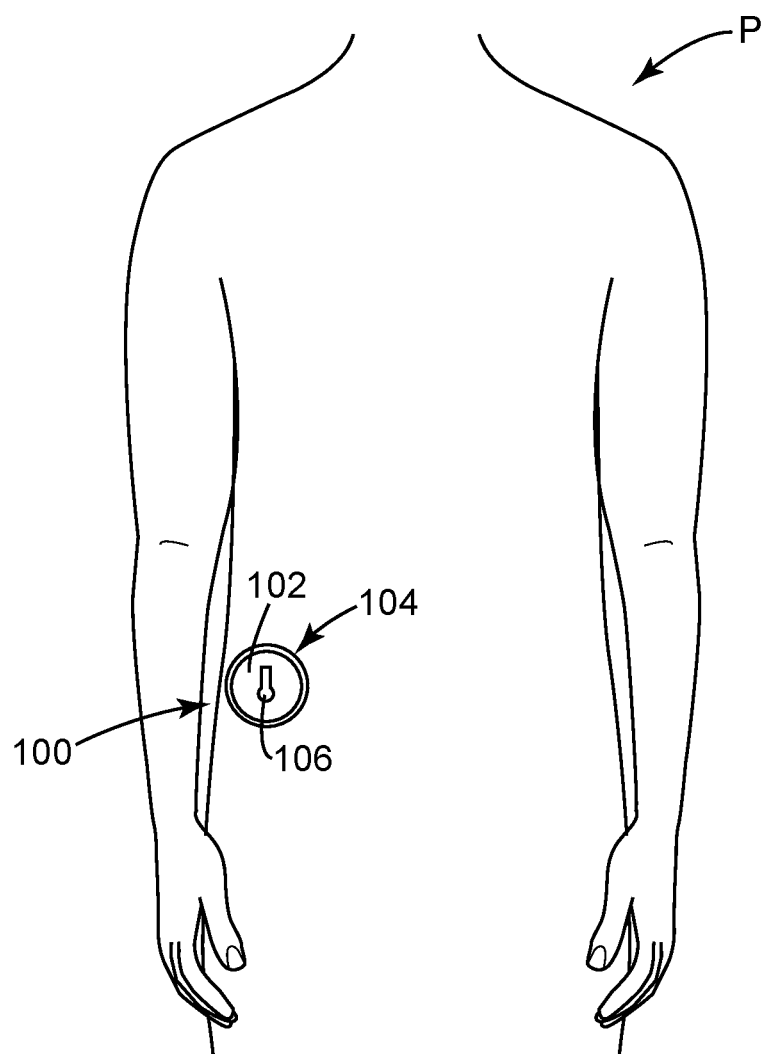
FIG. 1 depicts a sketch of an exemplary embodiment of a valve appliance in position on a patient.

Where applicable, like-reference characters designate identical or corresponding components and units throughout the several views (which are not to scale unless otherwise indicated). The embodiments disclosed herein may include elements that appear in one or more of the several views or in combinations of the several views. Methods are exemplary only and may be modified by, for example, reordering, adding, removing, and/or altering the individual stages.

DETAILED DESCRIPTION

The discussion that follows describes medical appliances that can engage with surgically-formed stoma on a patient. These appliances allow patients to periodically discharge waste from their bodies into a bag or a container for proper disposal. The design proposed, however, does not require much, if any, interaction by the patient to ensure that it properly engages with the stoma to minimize leaks or other inadvertent discharge of waste.

FIG. 1 depicts a sketch diagram of an exemplary embodiment of a valve appliance 100. This embodiment is shown on a patient P, typically at a location on patient P where access to a body cavity is necessary after a surgical procedure. This location may have a stoma, or port, which allows waste to exit patient P into a collection device like a bag or pouch (not shown). The appliance 100 may include a support unit 102 that receives a spigot 104. A seal unit 106 may reside on part of the support unit 102 to engage with the interior of the stoma.

The support unit 102 can be configured to provide access to discharge waste from the patient's body. These configurations may embody devices with a flowpath that receives waste from the stoma. These devices may have a low-profile, preferably one that can be discretely worn under the patient's clothing.

The spigot 104 can be configured to regulate waste discharge through the flowpath. These configurations may embody devices that can move (e.g., rotate) relative to the support unit 102. These devices may interface with the collection device. In use, the patient may couple the collection device to an end of the spigot 104. The patient can manipulate the spigot 104 to start flow of waste that discharges from the stoma into the collection device. When complete, the patient can manipulate the spigot 104 to cease flow, remove the collection device, and return to their daily activities.

The seal unit 106 can be configured to seal the support unit 102 to the stoma. These configurations may embody devices made of materials that "self-seal" to create a fluid-tight or fluid-proof barrier between surfaces on both the device and the stoma. Preferably, the material does not require interaction with the patient to create this barrier. Exemplary materials may expand (in size or volume) inside of the stoma, for example, in response to contact with fluid (or other hydraulic interactions). The material may also absorb fluids to prevent migration of waste out of the patient's body. These features significantly simplify use and maintenance because the patient can rapidly remove and replace the material as part of their regular care or maintenance of the appliance 100.

Figure 2:
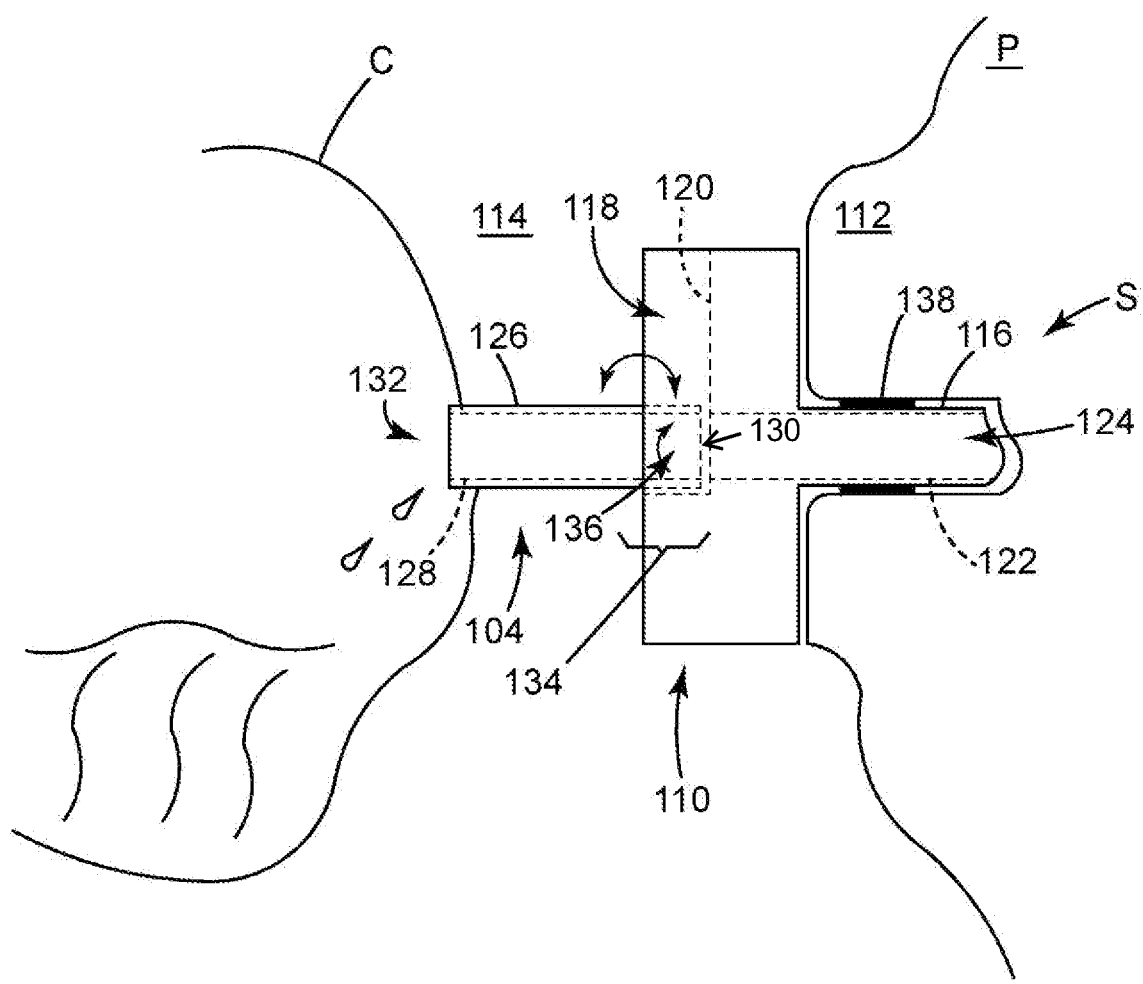
FIG. 2 depicts an elevation, side view of the valve appliance of FIG. 1.

FIG. 2 depicts a schematic diagram of an elevation view from the side of an example of the valve appliance 100 of FIG. 1. The support unit 102 may include a body 110 with a proximal side 112 and a distal side 114. The proximal side 112 may contact patient P with the appliance 100 in position at the stoma, shown and identified generally by the letter S. A stem 116 may extend from the proximal side 112. The stem 116 may form a cylinder that inserts into the stoma. The cylinder may form integrally with the body 110 as a single or monolithic piece. On the distal side 114, the body 110 may have a recess 118 that forms a back surface 120. A through-bore 122 may extend from the back surface 120 through the body 110 and the stem 116. The through-bore 122 creates a drain passage 124 for waste to exit patent P through stoma S.

Figure 3:
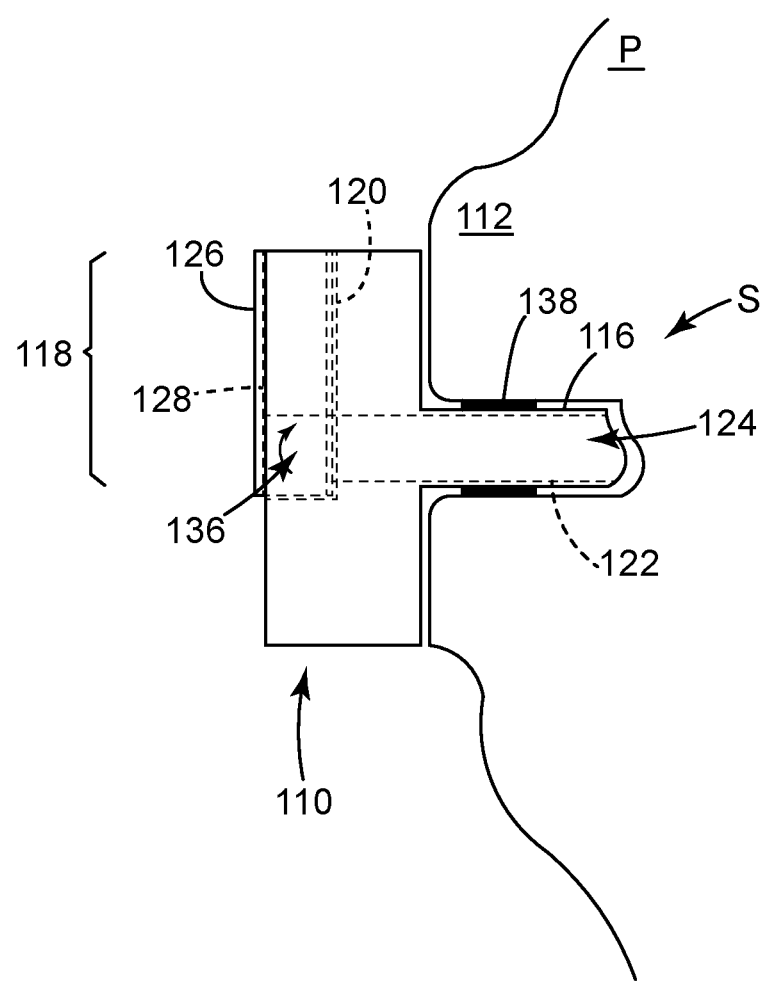
FIG. 3 depicts the side view of the valve appliance of FIG. 1, with the valve appliance in a different configuration.

The spigot 104 may be configured to fit into the recess 118. These configurations may comprise an elongated body 126, itself with a through-bore 128 that creates open ends (e.g., a first open end 130 and a second open end 132). The first open end 130 may insert into the cut-out recess 118, creating an articulating joint 134 with at least one degree of freedom (identified here as rotation about an axis 136). The axis 136 may extend perpendicular to the drain passage 124. A snug interference fit may be useful at the articulating joint 134 to retain the elongate body 126 in the recess 118, but not frustrate rotation about the axis 136. In use, the articulating joint 134 allows the elongated body 126 to change orientation relative to the body 110 to regulate flow of waste from stoma S. A first orientation for the elongated body 126 may align the through-bore 128 with the drain passage 124, as shown in FIG. 2. This orientation "opens" the appliance 100 to permit waste to flow into, for example, the collection device C that couples with the second open end 132 of the elongate body 126. As best shown in FIG. 3, rotation of the elongate body 126 to a second orientation causes misalignment of the through-bore 128 and the drain passage 124. This orientation "closes" the appliance 100 to block flow of waste out of stoma S. In this orientation, the elongate body 126 may fit into the recess 118 for it to stow out of the way when not "open" for use with collection bag C.

The seal unit 106 may be configured to fit onto the cylinder of the stem 116. These configurations may include a sleeve 138, for example, a hollow tube that can fit between the outer surface of the stem 116 and the inner wall of stoma S. The hollow tube may cover all or part of the stem 116. Suitable materials may include cotton, rayon, or other "tampon-like" materials that can absorb moisture or expand in size or shape. These materials may be suitable along or in combination with other materials (e.g., synthetic fibers like viscose rayon). In one implementation, the tube of material may form an annular seal with the inner wall of the stoma. This annular seal may secure or hold the appliance 100 in place (possibly to foreclose the need for a belt). It may also prevent leaks of waste from patient P, for example, from around the periphery of the stem 116. In one implementation, the sleeve 138 can be configured to allow an end user to remove a first tube of material from the stem 116 in favor of a second tube of material. This second tube of material may correspond with new material that replaces the soiled first tube of material. This feature allows the end user to clean and sterilize the appliance 100, as well as to maintain integrity (and cleanliness) of the sleeve 138 to avoid potential infection or other issues that may arise due to prolonged exposure of the sleeve 138 inside of stoma S.

Figure 4:
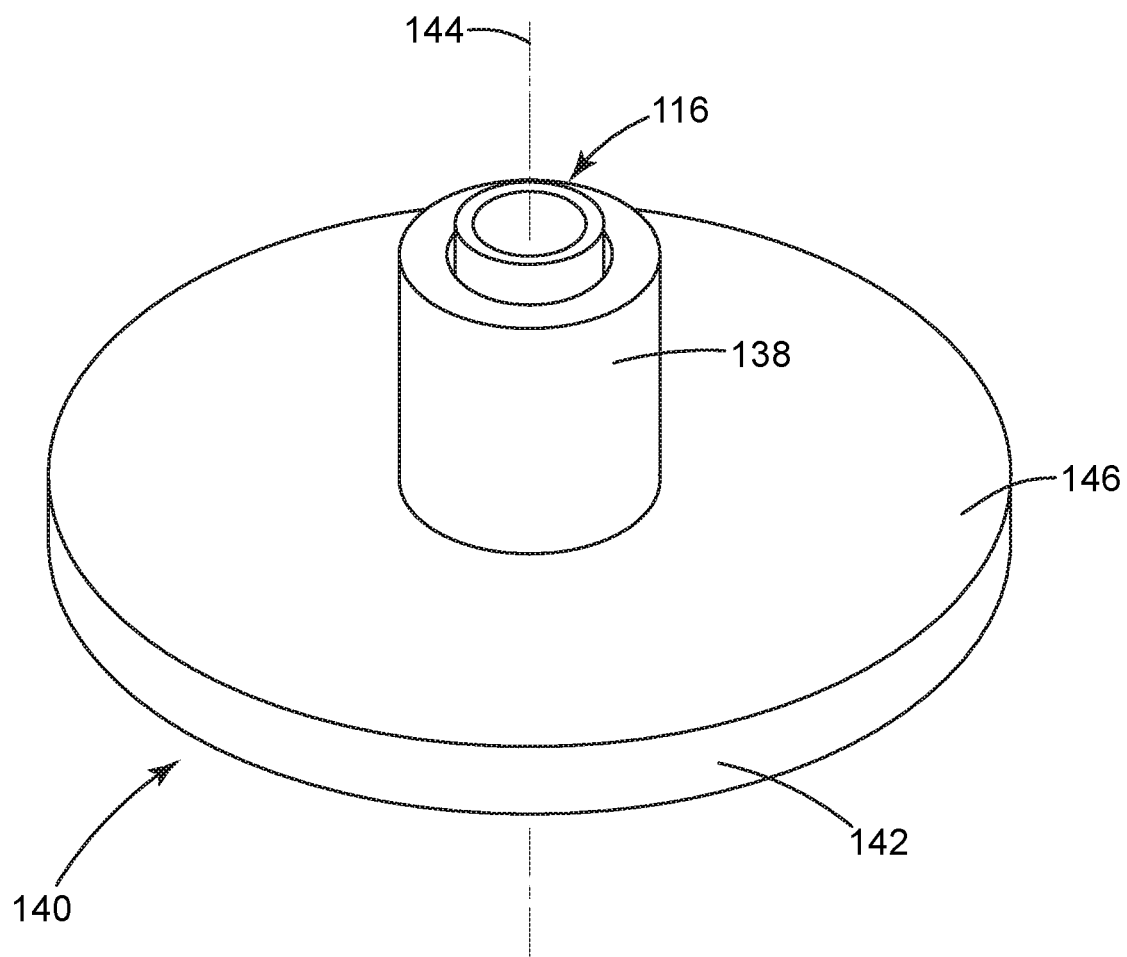
FIG. 4 depicts a perspective view from the top of an example of the valve appliance of FIG. 1.

FIG. 4 depicts a perspective view of exemplary structure for the body 110 for use in the valve appliance 100 of FIG. 1. This structure includes a disc portion 140 with an outer peripheral surface 142 that circumscribes an axis 144. The outer peripheral surface 142 may have an annular or circular shape, although other shapes, like a square, may also suffice. On the proximal side 112, the disc portion 140 may form a flat, planar surface 146, which as noted above may rest against patient P.

Figure 5:
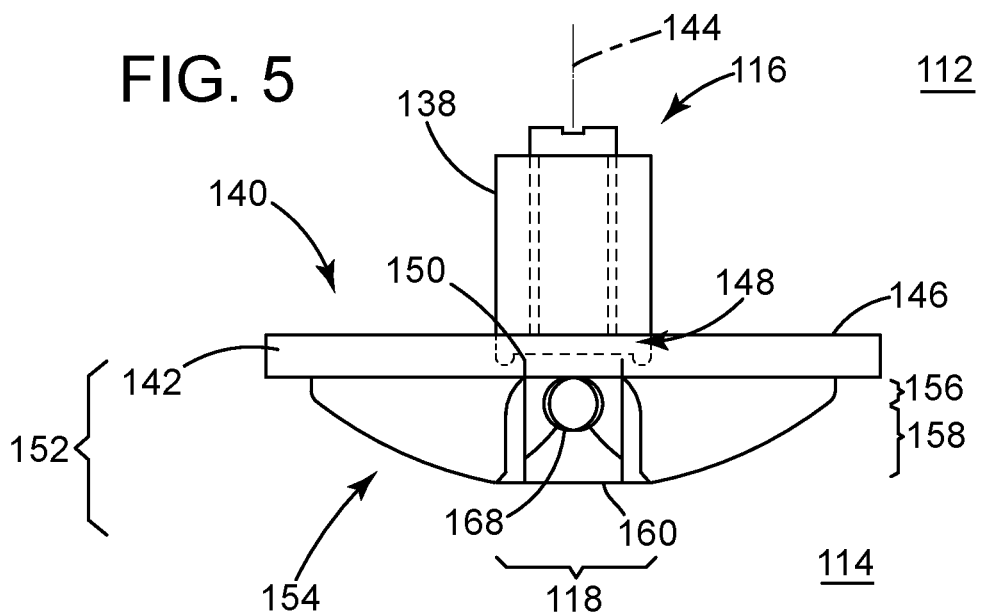
FIG. 5 depicts an elevation view from the side of the example of FIG. 4.

FIG. 5 shows an elevation view from the side of the example of FIG. 4. The surface 146 may include a shallow recess 148, for example, a circular cut-out or groove that aligns with (or circumscribes) the axis 144 and terminates at a bottom 150. Dimensions for the recess 148 may permit at least part of the sleeve 138 to set into the material of the disc portion 140. On the distal side 114, the body 110 may have a boss member 152 that resides on the disc portion 140, opposite the stem 116. The boss member 152 may have an outer surface 154 with a first portion 156 that is perpendicular or near-perpendicular with the axis 144. The first portion 156 terminates at a second portion 158, which has a generally domed or bulbous profile. This profile may flatten at top 160.

Figure 6:
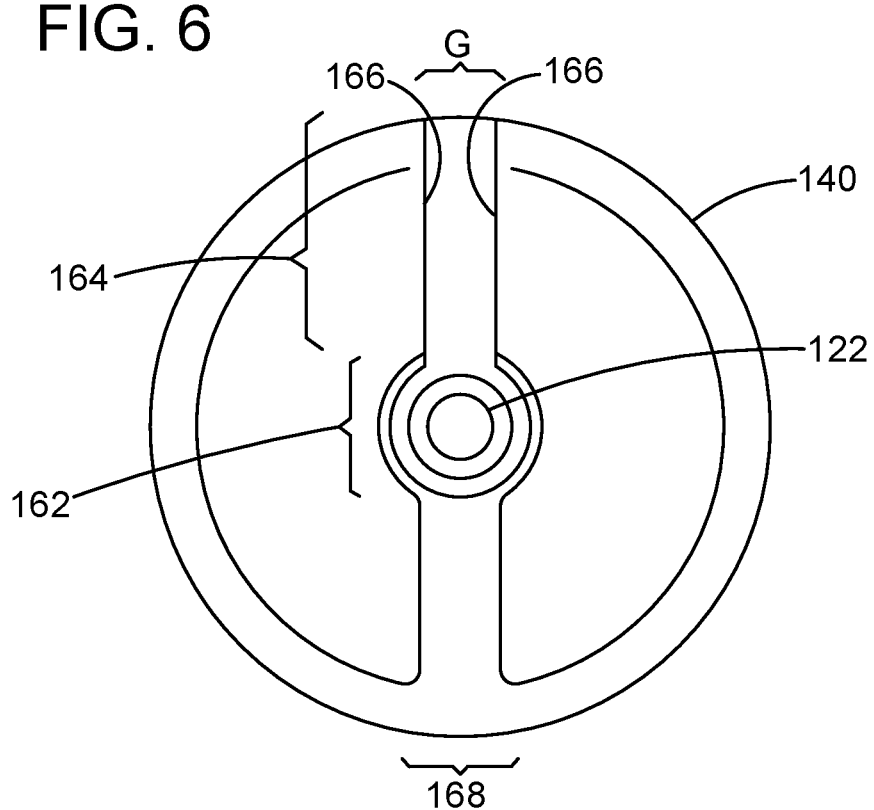
FIG. 6 depicts a plan view from the top of the example of FIG. 4.

With reference also to FIG. 6, which is a plan view of the proximal side 112 of the body 110, the recess 118 may have a first portion 162 that exposes the drain passage 124. Geometry for the first portion 162 may match corresponding geometry of the elongated body 126 of the spigot 104. The recess 118 may also have a second portion 164 that may extend radially outwardly from the first portion 162 to the perpendicular portion 156 of the outer surface 154. The second portion 164 may form opposite side walls 166 that are spaced apart from one another by a gap G. Examples of gap G are large enough to receive the elongated body 126 of the spigot 104. In one implementation, the body 110 may include an aperture 168 that extends in a direction opposite of the recess 118.

Figure 7:
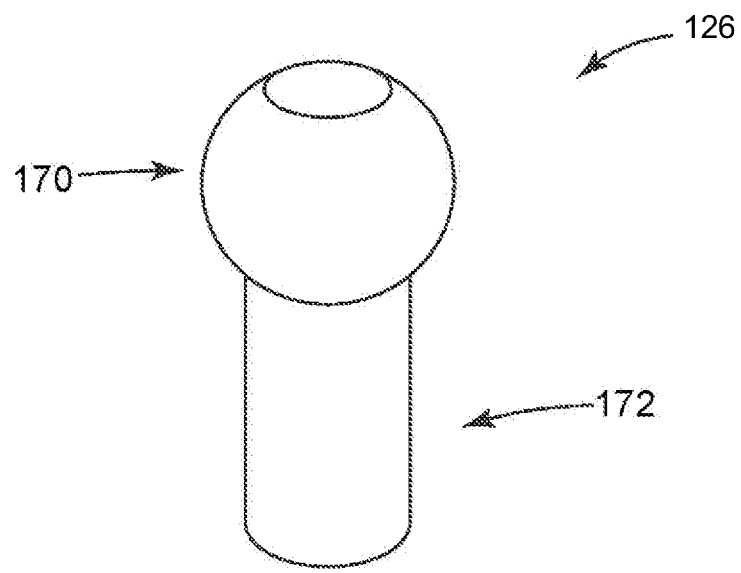
FIG. 7 depicts a perspective view of an example of a spigot for use in the example of FIG. 4.

FIG. 7 depicts a perspective view of an example of the elongated body 126 of the spigot 104. This example may have a bulbous, rounded portion 170 and a cylindrical portion 172. The rounded portion 170 may insert into the first portion 162 of the recess 118. As noted above, the fit may be snug, with appropriate tolerance interference to hold the elongated body 126 in position but still allow it to change orientation relative to the boss member 152.

Figure 8:
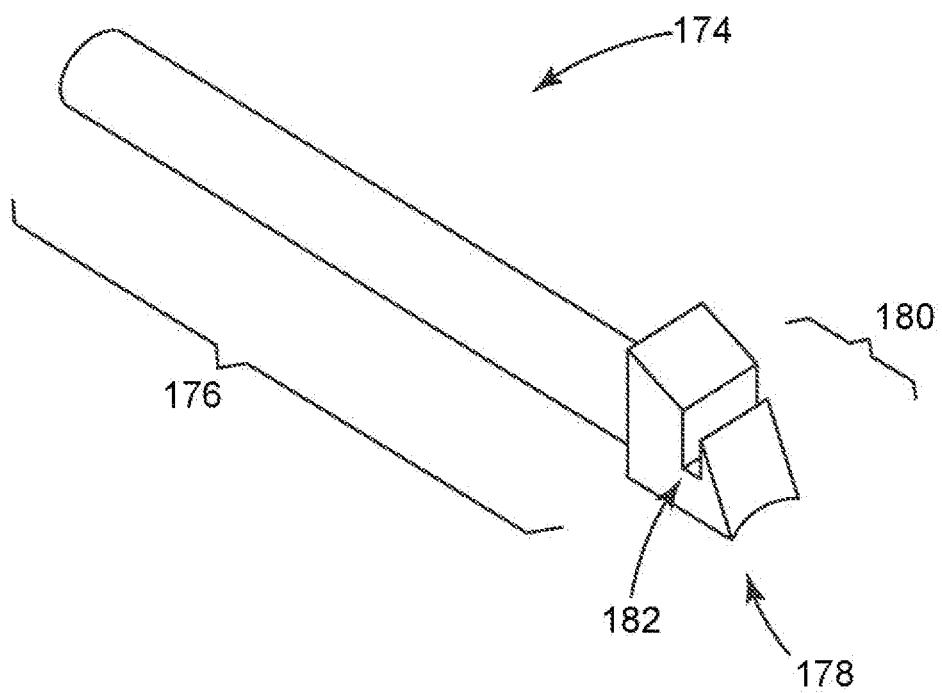
FIG. 8 depicts a perspective view of an example of a tool for use with the example of FIG. 4.

FIG. 8 depicts a perspective view of an example of a tool 174 for use with the appliance 100. The tool 174 may have an elongated, cylindrical body 176 that terminates at a locking feature 178. As shown, the locking feature 178 may form a chamfered head 180 that incorporates a slot 182. In use, the tool 174 may slide into the aperture 168 to engage with the rounded portion 170 of the elongate body 126. Engagement may prevent rotation of the spigot 104. In one example, the slot 182 may concomitantly engage with features on the body 110 to prevent the tool 174 from "backing out" of the aperture 168. Pressing on the chamfered head 180 can disengage the slot 182 and allow an end user to withdraw the tool 174. This feature frees the spigot 104 to move to its "open" orientation to allow waste to exit stoma S. The end user may also utilize the tool 174 to clean out the drain passage 124 to remove any waste that could block flow from stoma S.

Figure 9:
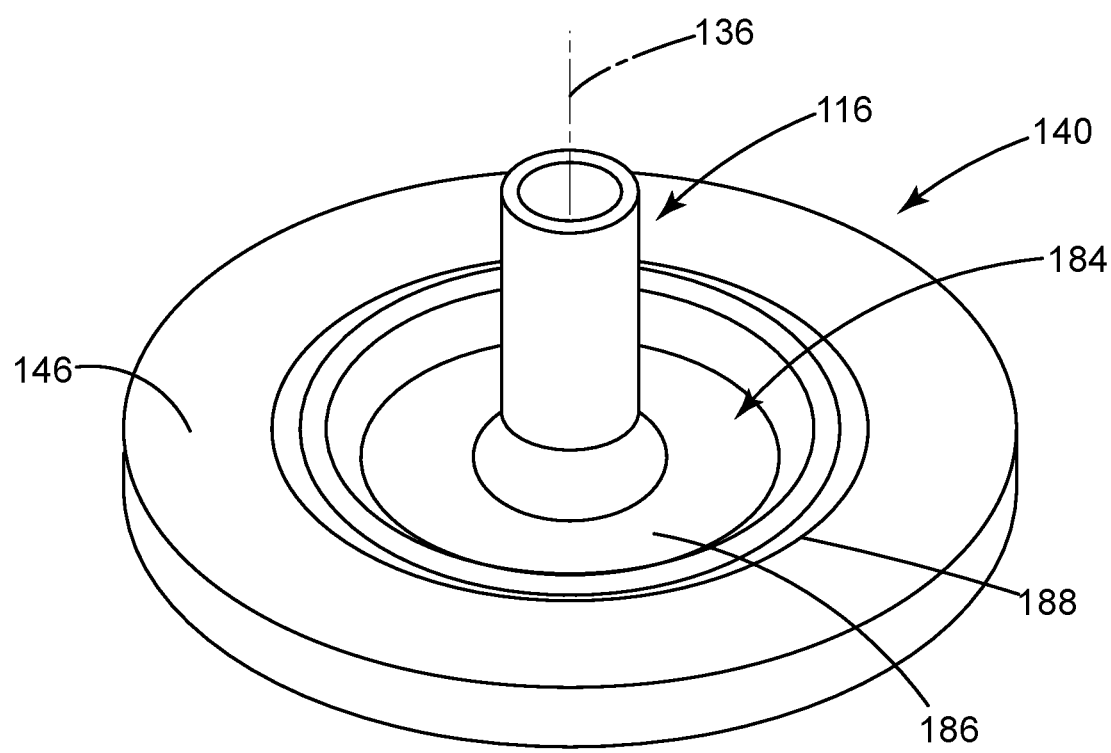
FIG. 9 depicts a perspective view of another example of the valve appliance of FIG. 1.
Figure 10:
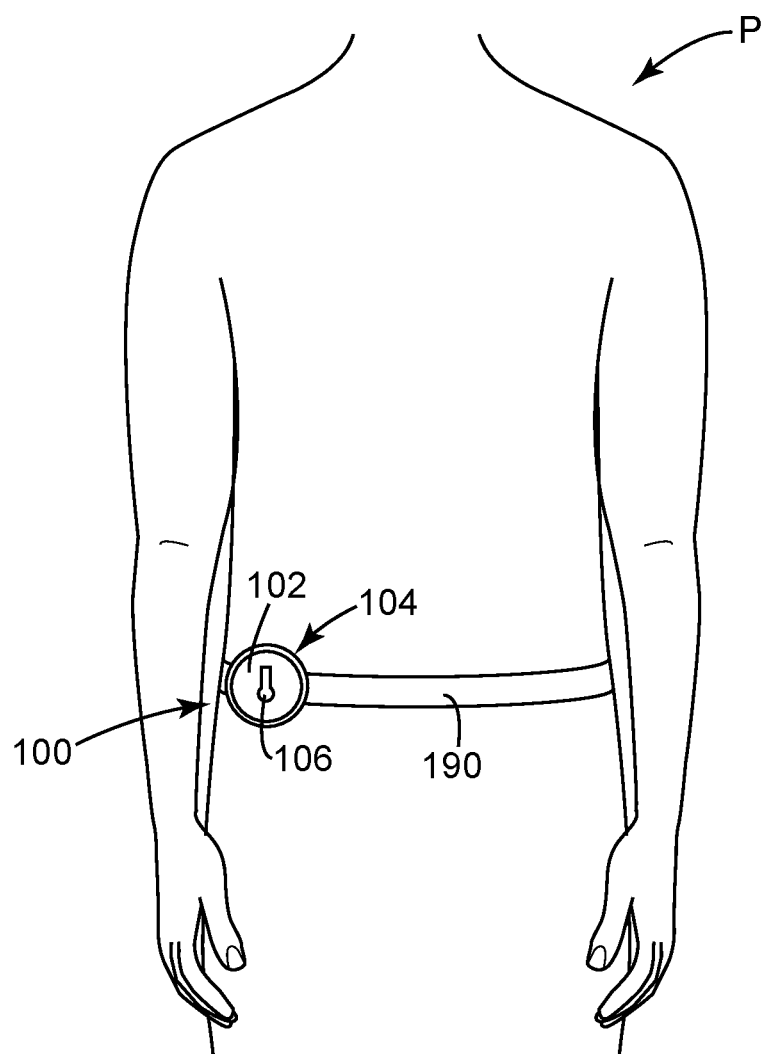
FIG. 10 depicts a sketch of the example of FIG. 9 on a patient.

FIG. 9 depicts a perspective view of another structure for the body 110 for use in the valve appliance 100 of FIG. 1. The flat surface 146 may include a central bore 184 that penetrates into the material to form a bottom 186. An annular groove 188 may circumscribe the bore 184. In one implementation, the seal unit 106 may include an o-ring or gasket that fits into the annular groove 188. A thin membrane made of compliant, flexible material may be useful to interpose between the flat surface 146 and patient P. These materials can prevent irritation of the skin of patient P under direct contact from the body 110 for long periods of time. As best shown in FIG. 10, a belt 190 may be required to secure the appliance 100 in place to allow patient P to carry on with daily functions.

In view of the foregoing, the improvements discussed herein can facilitate discharge of waste from stoma. The embodiments employ materials that self-seal with surfaces inside of the patient's body. This feature eliminates the need for the patient to interact with the device to properly affix it in position so as to avoid leaks or other potential mistakes that can allow waste to inadvertently discharge from the stoma.

This written description uses examples to disclose the invention, including the best mode, and also to enable any person skilled in the art to practice the invention, including making and using any devices or systems and performing any incorporated methods. An element or function recited in the singular and proceeded with the word "a" or "an" should be understood as not excluding plural said elements or functions, unless such exclusion is explicitly recited. References to "one embodiment" of the claimed invention should not be interpreted as excluding the existence of additional embodiments that also incorporate the recited features. Furthermore, the claims are but some examples that define the patentable scope of the invention. This scope may include and contemplate other examples that occur to those skilled in the art. Such other examples are intended to be within the scope of the claims if they have structural elements that do not differ from the literal language of the claims, or if they include equivalent structural elements with insubstantial differences from the literal language of the claims.

Examples appear below that include certain elements or clauses one or more of which may be combined with other elements and clauses describe embodiments contemplated within the scope and spirit of this disclosure.

What is claimed is:

1. A medical appliance, comprising:
    a support unit comprising a body portion with a first side and a second side, the first side includes a stem extending transversely away from the body portion, the second side comprising a recess, wherein the body portion comprises an annular disc having a first side and a second side, and the stem comprises a first cylindrical member coupled with the first side;
    a moveable spigot inserted into the recess, the moveable spigot comprising a second cylindrical member coupled with the second side, the second cylindrical member rotatable relative to the annular disc, wherein the second cylindrical member has a first position that forms a flow path through the first cylindrical member and the annular disc; and
    a seal unit disposed on the stem, the seal unit comprising material that expands to create a barrier to fluid flow and further comprising a hollow tube circumscribing the first cylindrical member, the hollow tube comprising material that is both absorbent and expandable.

2. The medical appliance of claim 1, wherein the moveable spigot has an end rotatably received in the recess and said spigot rotates in only one plane between open and closed positions.

3. The medical appliance of claim 1, wherein the second cylindrical member is rotatable from the first position to a second position that terminates the flow path in the annular disc.

4. The medical appliance of claim 3, wherein the second cylindrical member is received in a recess in the annular disc and rotates around an axis lying within the annular disc.

5. The medical appliance of claim 1, wherein the first side of the annular disc defines an annular groove surrounding the first cylindrical member, and said medical appliance further comprises a gasket disposed in said annular groove.

6. The medical appliance of claim 1, wherein the hollow tube material extends into the disc portion.

7. The medical appliance of claim 1, wherein insertion of the first cylindrical member into a stoma on a patient causes the hollow tube material to directly contact an interior wall of stoma.

8. A medical appliance, comprising:
    a support unit comprising a body portion with a first side and a second side, the first side includes a stem extending transversely away from the body portion, the second side comprising a recess;
    a moveable spigot inserted into the recess; and
    a seal unit disposed on the stem, the seal unit comprising material that expands to create a barrier to fluid flow;
    wherein the moveable spigot has an elongated body with a bulbous end that presses into the recess to form an articulating joint whereby articulation of said joint opens and closes the spigot.

9. The medical appliance of claim 8, wherein the seal unit forms a hollow tube that circumscribes the stem.

10. The medical appliance of claim 8, wherein the seal unit is removeably replaceable from the stem.

11. The medical appliance of claim 8, wherein the material is absorbent.

12. The medical appliance of claim 8, wherein the material contacts an inner surface of a stoma on a patient with the stem in position in the stoma.

13. The medical appliance of claim 8, wherein the body portion comprises a groove around the stem to receive at least part of the seal unit.

14. The medical appliance of claim 8, wherein the body portion has a domed boss member that forms the recess.

15. The medical appliance of claim 8, further comprising a tool that extends perpendicular to the stem through the body portion to engage with the moveable spigot.

* * * * *